(12) United States Patent
Eaton et al.

(10) Patent No.: US 8,744,875 B2
(45) Date of Patent: Jun. 3, 2014

(54) SYSTEMS AND METHODS FOR SYNCHRONIZING DATA OF A PATIENT MONITOR AND A PORTABLE SENSOR MODULE

(75) Inventors: Scott Eaton, Briarcliff Manor, NY (US); James Fidacaro, Mountain Lakes, NJ (US); Frank Menzel, Oakland, NJ (US); Jack Balji, Mahwah, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 756 days.

(21) Appl. No.: 12/646,599

(22) Filed: Dec. 23, 2009

(65) Prior Publication Data

US 2011/0152629 A1  Jun. 23, 2011

(51) Int. Cl.
*G06Q 50/22* (2012.01)
*G06Q 50/24* (2012.01)

(52) U.S. Cl.
USPC .................................................. 705/3; 705/2

(58) Field of Classification Search
CPC ............................... G06Q 50/22; G06Q 50/24
USPC ......................................................... 705/2–3
See application file for complete search history.

(56) References Cited

U.S. PATENT DOCUMENTS

| | | | | |
|---|---|---|---|---|
| 5,375,604 A | * | 12/1994 | Kelly et al. | 600/484 |
| 5,640,953 A | * | 6/1997 | Bishop et al. | 600/300 |
| 8,169,304 B2 | * | 5/2012 | Schuman et al. | 340/286.07 |
| 8,174,912 B2 | * | 5/2012 | Warren | 365/189.16 |
| 2005/0033124 A1 | * | 2/2005 | Kelly et al. | 600/300 |

* cited by examiner

*Primary Examiner* — Michael Fuelling
(74) *Attorney, Agent, or Firm* — Kory D. Christensen; Stoel Rives LLP

(57) ABSTRACT

A patient monitor is synchronized with a portable sensor module by detecting a first coupling of the portable sensor module to the patient monitor. In response to the first coupling, the portable sensor module and the patient monitor each store configuration settings and record patient data acquired through the portable sensor module. After the portable sensor module is decoupled from the patient monitor, the portable sensor module continues to store patient data and the configuration settings stored in the patient monitor and the portable sensor module are allowed to change relative to one another. Upon detecting a second coupling of the portable sensor module to the patient monitor, the portable sensor module and the patient monitor resynchronize with one another to remove any differences in the configuration settings and to provide copies of any patient data missing from either the portable sensor module and the patient monitor.

9 Claims, 8 Drawing Sheets

SYSTEMS AND METHODS FOR SYNCHRONIZING DATA OF A PATIENT MONITOR AND A PORTABLE SENSOR MODULE

TECHNICAL FIELD

The present disclosure relates to patient monitor systems.

DETAILED DESCRIPTION

Figure 1:
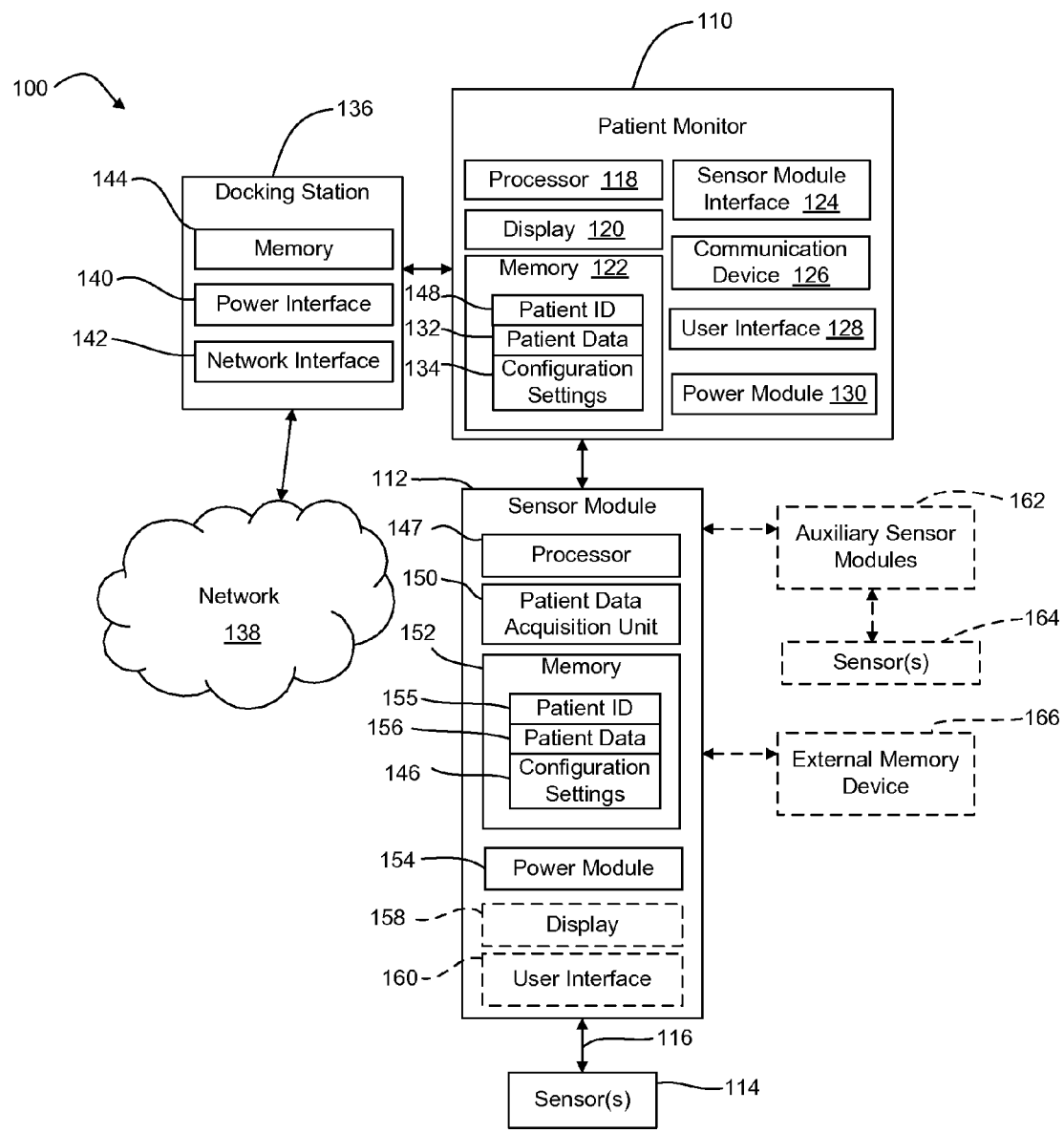
FIG. 1 is a block diagram of a patient monitoring system according to one embodiment.

Patient monitors are used to acquire, analyze, and display data from sensors attached to a patient. The data may include, for example, pulse, temperature, respiration, blood pressure (e.g., non-invasive blood pressure (NIBP)), blood oxygen (e.g., saturation of peripheral oxygen ($SpO_2$)), electrocardiogram (ECG), and other patient parameters. It is often desirable to continuously monitor patient parameters when transporting patients, including while transporting patients between hospital wards. Transporting patients between hospital wards, however, may require users such as nurses or other hospital staff to spend time and effort reattaching the patient from a portable monitoring system to a fixed monitoring system.

After transporting a patient to and from locations within a hospital, users may also spend time and effort reconfiguring a patient monitor with configuration settings for the particular patient, for default configuration settings used by the different wards, and/or for configuration settings based on user preferences. The configuration settings used for a particular patient may depend on the particular patient's condition such as current symptoms (e.g., heart rate, temperature, etc.), diagnosed diseases, demographics (e.g., age, sex, weight, etc.), and other patient conditions. The default configuration settings may be defined, for example, by administrators of each ward and may be based on hospital-specific practices and/or general (e.g., statewide or nationwide) standard practices. For example, an emergency room may be required to monitor a different set of patient parameters or use different display settings (e.g., brightness or colors) than that of a catheterization lab or an intensive care unit.

Thus, when a patient is connected to a fixed patient monitor or when a portable patient monitor is introduced into a patient ward, the patient monitor generally needs to be reconfigured. This may be accomplished, for example, by accessing the patient monitor's menu system and configuring the patient monitor. Alternatively, the patient monitor may be configured by downloading a configuration from an external storage device or from a network. The configuration process can be time consuming. If it is required to manually load the configuration data from a storage device or a network, the user may forget to load the configuration data and the patient monitor will not be set correctly for the particular patient or for the ward's custom configuration. If the user is required to enter the configuration data manually into the patient monitor, the configuration process may also be error prone.

Thus, in one embodiment, a portable sensor module is configured to store configuration settings and patient data and to synchronize the configuration settings and patient data with a patient monitor when a patient is transported from ward to ward or from one bed to another bed within a ward. The portable sensor module receives patient data from leads connected to sensors attached to the patient and is configured to be selectively coupled to the patient monitor. When coupled to one another, both the patient monitor and the sensor module store the patient data received from the sensors and the configuration settings used by the patient monitor. To transport a patient, the sensor module is decoupled from the patient monitor and transported with the patient such that the sensors and leads may remain with the patient. During transport, the patient monitor continues acquiring and storing the patient data. Upon being reconnected to the original patient monitor, or to a different patient monitor, the sensor module synchronizes its data and configuration settings with that of the coupled patient monitor.

For example, the sensor module may be configured to store the most recent 12 hours of patient data and one or more patient monitors may be configured to store the most recent 48 hours of patient data. In other words, in this example, the sensor module acts like a 12 hour circular buffer and the one or more patient monitors act like 48 hour circular buffers. If the patient is moved from a hospital ward to an intensive care unit (ICU) for 8 hours for closer observation, then a user may decouple the sensor module from a first patient monitor and move it with the patient. Upon arrival in the ICU, the user may couple the sensor module to a second patient monitor. The second patient monitor then begins displaying and recording newly acquired patient data received through the sensor module (and any auxiliary modules) and uploads the most recent 12 hours (assuming that the patient has been monitored for at least 12 hours) of patient data from the sensor module (including data acquired by the sensor module during transport). In certain embodiments, the second patient monitor also allows the user to selectively update some or all its configuration settings with the configuration settings stored in the sensor module. Upon return to the original ward, the first patient monitor displays and records newly acquired patient data and uploads the previous 8 hours of patient data from the sensor module (for which it has a gap in its data according to this example). The first patient monitor may also allow the user to update any configuration settings that changed on the sensor module.

In certain embodiments, the sensor module is configured to communicate with an external memory device for increasing the amount of patient data transferred with the patient. Referring again to the example above where the sensor module acts as a 12 hour circular buffer, the patient may actually remain in the ICU for 24 hours. In this case, the second patient monitor would include the most recent 24 hours of patient data but the sensor module would only include the most recent 12 hours of patient data. Thus, the user may attach (e.g., through a universal serial bus (USB) or other interface) an external memory device to sensor module to capture patient data that exceeds the 12 hour limit or to download the extra data stored on the second patient monitor. When the patient is transported back to the original ward, the user transports both the sensor module and the external memory device with the patient such that all 24 hours (in this example) of patient data may be synchronized with the first patient monitor.

In addition, or in other embodiments, the sensor module may be configured to receive and record patient data from one or more auxiliary sensor modules. For example, in one embodiment, the sensor module may interface directly with sensor leads for certain types of patient data such as ECG, $SpO_2$, NIBP, and/or temperature, and the sensor module may receive $CO_2$ data from an external $CO_2$ module.

In addition, or in other embodiments, the sensor module may be configured to provide basic patient monitor functionality as it is transported with a patient from one location to another. For example, the sensor module may include a small liquid crystal display (LCD) or other display screen. The sensor module may include a basic user interface (UI) that allows the user to view at least some of the configuration settings, alarm settings, and patient data values. The display screen and user interface may also provide information such as a patient identifier (ID), sensor module ID, sensor ID(s), user ID, and last coupled patient monitor ID. The display screen and/or user interface may also allow the user to silence an alarm or enter user data. To maintain the portability of the sensor module and/or to reduce costs, in certain embodiments, the display screen and user interface of the sensor module provide limited functionality for use during transporting patients. For example, the user may not be able to configure alarms in certain embodiments of the display screen and user interface of the sensor module.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

FIG. 1 is a block diagram of a patient monitoring system 100 according to one embodiment. The patient monitoring system 100 includes one or more patient monitors 110 (one shown) and a sensor module 112. The sensor module 112 is mobile to allow patients to be continuously monitored during transportation between different wards or monitoring locations without being disconnected from one or more sensors 114 and associated leads 116. Accordingly, the sensor module 112 is configured to be selectively coupled with and selectively decoupled from the patient monitor 110.

The patient monitor 110, according to the example embodiment illustrated in FIG. 1, includes a processor 118, a display device 120, a memory device 122, a sensor module interface 124, a communication device 126, a user interface 128, and a power module 130. The processor 118 is configured to process patient data signals received through the sensor module interface 124 and to display the patient data signals (e.g., as waveforms and/or numerical readouts) on the display device 120. The sensor module interface 124 receives the patient data signals through the sensor module 112 from the one or more sensors 114 attached to a patient (not shown). The sensor module interface 124 may be configured to process the acquired patient data signals in cooperation with the processor 118.

For illustrative purposes, the patient monitor 110 is shown as being coupled to a docking station 136. In certain embodiments, the docking station 136 provides the patient monitor 110 with power and/or a connection to a network 138, such a hospital's local area network (LAN) and/or the Internet. Accordingly, the docking station 136 is illustrated as including a power interface 140 and a network interface 142. The power interface 140 may be configured to convert an alternating current (AC) power signal to a direct current (DC) power signal and/or provide power signal conditioning for the coupled patient monitor 110. The network interface 142 may include, for example, an Ethernet communication controller to allow the coupled patient monitor 110 to communicate through the network 138 through the docking station 136. The network interface 142 may be associated with a media access control (MAC) address. The docking station 136 also includes a memory device 144 to store, among other data, default configuration settings (not shown).

The patient monitor 110 may store the patient data signals as patient data 132 in the memory device 122 along with other data. For example, the patient monitor 110 may store a current set of configuration settings 134 in the memory device 122. In one embodiment, the patient monitor 110 replaces the current set of configuration settings in the memory device 142 with configuration settings 146 stored in the sensor module 112, with the default configuration settings stored in or received through the docking station 136 corresponding to a particular hospital ward, and/or with user entered (e.g., selected through the user interface 128) configuration settings corresponding to the particular patient's condition and/or user preferences. The memory device 122 may also include a patient ID 148, which may include an index of patient IDs, used to correlate portions of the patient data 132 and/or the configuration settings 134 with particular patients. Thus, different portions of the patient data 132 and/or the configuration settings 134 may correspond to different patient IDs 148.

The communication device 126 is configured to communicate with the network 138 through the network interface 142 of the docking station 136. In certain embodiments, the communication device 126 is also configured to wirelessly communicate with the network 138 when the patient monitor 110 is not coupled to the docking station 136.

The power module 130 receives a power signal from the power interface 140 of the docking station 136. The power module 130 provides any necessary power conversions and distributes power throughout the patient monitor 110. The power module 130 may include a battery that is charged through the power interface 140 while the patient monitor 110 is coupled to the docking station 136.

The sensor module interface 124 cooperates with the processor 118 to detect a coupling of the patient monitor 110 to the sensor module 112. In response to the patient monitor 110 coupling with the sensor module 112, the sensor module interface 124 prompts the user (e.g., through the user interface 128) to select one or more of the configuration settings 146 stored in the sensor module 112. If the user declines to use the configuration settings 146 stored in the sensor module 112, the sensor module interface 124 updates the configuration settings 146 of the sensor module 112 with the current configuration settings 134 of the patient monitor 110. When coupled to the sensor module 112, the sensor module interface 124 also updates the configuration settings 146 of the sensor module 112 with any changes made by the user to the current configuration settings 134 of the patient monitor 110.

An artisan will recognize from the disclosure herein that the processor 118 and/or the sensor module interface 124 either combined or separately, may include a special purpose processor configured to perform the processes described herein. In another embodiment, the processor 118 and/or sensor module interface 124, either combined or separately, may include a general purpose processor configured to execute computer executable instructions (e.g., stored in a computer-readable medium such as the memory device 122) to perform the processes described herein.

The sensor module 112 includes a processor 147, a patient data acquisition unit 150, a memory device 152, and a power module 154. The processor 147 is configured to execute computer executable instructions (e.g., stored in a computer-readable medium such as the memory device 152) to perform the processes described herein. The memory device 152 may store a patient ID 155 for synchronizing data for particular patients as discussed herein. The patient data acquisition unit 150 is configured to receive the patient data signals from the sensors 114 through the leads 116. The patient data acquisition unit 150 may be configured to receive and store different types of patient data signals. For example, the patient data acquisition unit 150 may include different card, modules or circuitry for sensing ECG, $SpO_2$, NIBP, and/or temperature data. The patient data acquisition unit 150 stores the patient data signals as patient data 156 in the memory device 152 and (when coupled to the patient monitor 110) communicates the patient data signals to the patient monitor 110 (e.g., in real-time). During synchronization, the patient data acquisition unit 150 also communicates the stored configuration settings 146 to the patient monitor.

The power module 154 may include a battery (not shown) that allows the sensor module 112 to be used in a mobile mode when transporting a patient. The power module 154 may also include circuitry (not shown) for charging the battery and/or operating the sensor module 112 with power received from the power module 130 of the patient monitor 110 and/or the power interface 140 of the docking station 136.

In one embodiment, the sensor module 112 further includes a display device 158 and a user interface 160 that allow the sensor module 112 to operate in a monitor mode. When decoupled from the patient monitor 110, for example, the sensor module 112 may function with limited monitor capabilities. As discussed above, the display device 158 may include a small LCD or other display screen. The user interface 160 allows the user to view at least some of the configuration settings, alarm settings, and patient data values. The display device 158 and the user interface 160 may also provide information such as a patient ID, sensor module ID, sensor ID(s), user ID, and last coupled patient monitor ID. The display device 158 and/or the user interface 160 may also allow the user to silence an alarm or enter user data. To maintain the portability of the sensor module 112 and/or to reduce costs, in certain embodiments, the display device 158 and the user interface 160 of the sensor module 112 provide limited functionality for use during transporting patients. For example, in certain embodiments, the user may not be able to configure alarms through the sensor module 112.

In addition, or in another embodiment, the sensor module 112 may be configured to receive and record patient data from one or more auxiliary sensor modules 162. The one or more auxiliary sensor modules 162 may acquire patient data signals from one or more auxiliary sensors 164 attached to a patient. For example, in one embodiment, the one or more auxiliary sensor modules 162 may include a $CO_2$ module. The sensor module 112 is configured to store the patient data signals received from the one or more auxiliary sensor modules 162 with the patient data 156 in the memory device 152 and to provide the patient data signals received from the one or more auxiliary sensor modules 162 to the patient module for storage as patient data 132 in the memory device 132. An artisan will recognize from the disclosure herein that in other embodiments the one or more auxiliary sensor modules 162 may communicate directly with the patient monitor 110, and that the sensor module 112 may receive patient data from the one or more auxiliary sensor modules 162 through the patient monitor 110.

In addition, or in other embodiments, the sensor module 112 may be configured to communicate with an external memory device 166. As discussed above, the sensor module 112 may use the external memory device 166 to increase its capacity to store the patient data 152. In certain embodiments, the external memory device 166 may be considered an extension of a circular buffer used to store the patient data 156.

Figure 2:
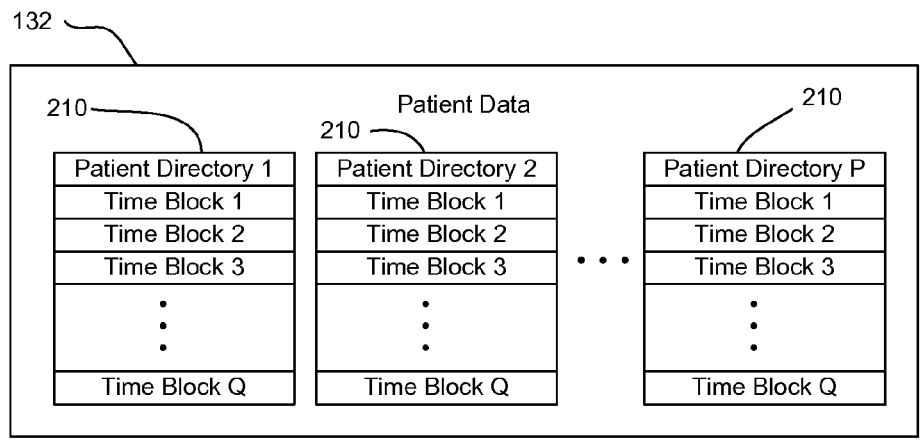
FIG. 2 graphically represents a data structure of patient data stored in the patient monitor illustrated in FIG. 1 according to one embodiment.

FIG. 2 graphically represents a data structure of the patient data 132 stored in the patient monitor 110 illustrated in FIG. 1 according to one embodiment. A similar data structure may be used for the patient data 156 stored in the sensor module 112. In certain embodiments, however, the patient monitor 110 is configured to store patient data 132 for a plurality of patients and the sensor module 112 is configured to store patient data 156 for a single patient (e.g. a current patient).

In the example embodiment shown in FIG. 2, the patient data 132 is organized by patient directories 210. Each patient directory 210 corresponds to a respective unique patient ID 148. In this example, the patient data 132 includes a total of P patient directories 210. Thus, the memory device 122 of the patient monitor 110 may store patient data 132 for a plurality of different patients (e.g., P number of patients). A patient monitor 110 with 72 hours of storage capacity, for example, may store 12 hours of data for a first patient, 24 hours of data for a second patient, 24 hours of data for a third patient, and 12 hours of data for a fourth patient. When a sensor module corresponding to one of these four patients (based on the patient ID 148) is reconnected to the patient monitor 110, synchronized and newly acquired patient data 132 is added to the corresponding patient directory 210. If the 72 hours of storage capacity is full (as in this example), the patient monitor 110 according to one embodiment reassigns memory blocks from another patient directory (e.g., with the oldest data) to the patient directory 210 corresponding to the current patient ID 148. Once all of the memory blocks are reassigned to the patient directory 210 corresponding to the current patient ID 148, the patient monitor 110 behaves as a circular buffer and overwrites the oldest data corresponding to the current patient ID 148. An artisan will recognize from the disclosure herein that patient data 132 for more than four or fewer than four patients may also be stored.

The patient data 132 in each patient directory 210 is divided into a plurality of time blocks (e.g., Q time blocks) or files to facilitate transfer of data between the patient monitor 110 and the sensor module 112, and vice-versa. System resources are managed more efficiently by transferring smaller files as compared to transferring a single file with 12 hours to 72 hours of data. Thus, in certain embodiments, the patient data 132 is divided into time blocks of 30 minutes, 60 minutes, or another time interval that allows efficient data management. During synchronization or acquisition of new patient data, files including 30 minutes or 60 minutes of data are exchanged between sensor module 112 and the patient monitor 110.

Figure 3A:
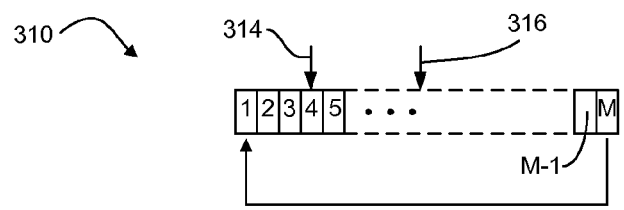
FIGS. 3A and 3B graphically represent a circular buffer for the sensor module and a circular buffer for the patient monitor for storing patient data according to one embodiment.
Figure 3B:
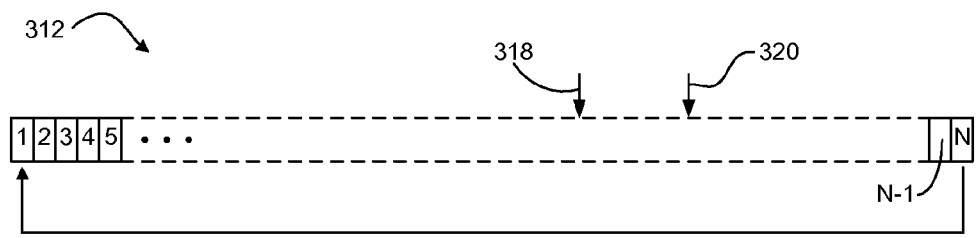

FIGS. 3A and 3B graphically represent a circular buffer 310 for the sensor module 112 and a circular buffer 312 for the patient monitor 110 for storing patient data according to one embodiment. The circular buffer 310 for the sensor module 112 includes a total of M memory blocks and the circular buffer 312 for the patient monitor 110 includes N memory blocks. In this example embodiment, the circular buffer 310 for the sensor module 112 is illustrated with less memory blocks than the circular buffer 312 for the patient monitor 110. For example, the circular buffer 310 for the sensor module 112 may have a sufficient number of memory blocks to store approximately 12 hours of patient data 156 and the circular buffer 312 for the patient monitor 110 may have a sufficient number of memory blocks to store approximately 72 hours of patient data 132. An artisan will recognize from the disclosure herein, however, that the sensor module 112 and the patient monitor 110 may also be configured to store approximately equal amounts of patient data or that the sensor module 112 may be configured to store more patient data than that stored in the patient monitor 110.

In one embodiment, the patient data stored in each memory block in each circular buffer 310, 312 is time stamped for synchronization between the patient monitor 110 and the sensor module 112. Thus, based on the respective time stamps, the patient monitor 110 and the sensor module 112 can determine which memory blocks to exchange such that each includes its respective limit of the most recent patient data available. For example, the patient monitor 110 may determine from the time stamps that the sensor module 112 includes patient data missing from the patient monitor 110 on a certain date between the hours of 4:15 P.M. and 8:30 P.M. Accordingly, the patient 110 monitor may retrieve the corresponding patient data from the circular buffer 310 of the sensor module 112 to store in its own circular buffer 312. In certain such embodiments, the patient monitor 110 saves the patient data acquired from the sensor module 112 in memory blocks corresponding to the time period of 4:15 P.M. to 8:30 P.M. such that newly acquired data may be stored in memory blocks corresponding to 8:30 P.M onward. This same example may also apply to transferring patient data from the patient monitor 110 to the sensor module 112 (e.g., when a new sensor module is used for a patient with historical data already stored in the patient monitor 110).

In another embodiment, markers 314, 316, 318, 320 are used to indicate the locations within each circular buffer 310, 312 that correspond to coupling or decoupling of the patient monitor 110 and the sensor module 112. For example, the marker 314 indicates where a decoupling occurred with respect to the circular buffer 310 of the sensor module 112. A corresponding marker 318 indicates where this same decoupling event occurred with respect to the circular buffer 312 of the patient monitor 110. Similarly, the markers 316 and 320 indicate where a reconnection or coupling event occurred between the patient monitor 110 and the sensor module 112. Because different patient monitors 110 may be connected to different sensor modules 112, the markers 314, 316 may include unique patient monitor identifiers and the markers 318, 320 may include unique sensor module and/or patient identifiers. During synchronization in this example, patient data stored in the memory blocks of the circular buffer 310 between the markers 314 and 316 may be copied to the memory blocks of the circular buffer 312 between the markers 318 and 320, and newly acquired patient data may be added to the circular buffers after (e.g., to the right of) the respective markers 316 and 320.

Figure 4:
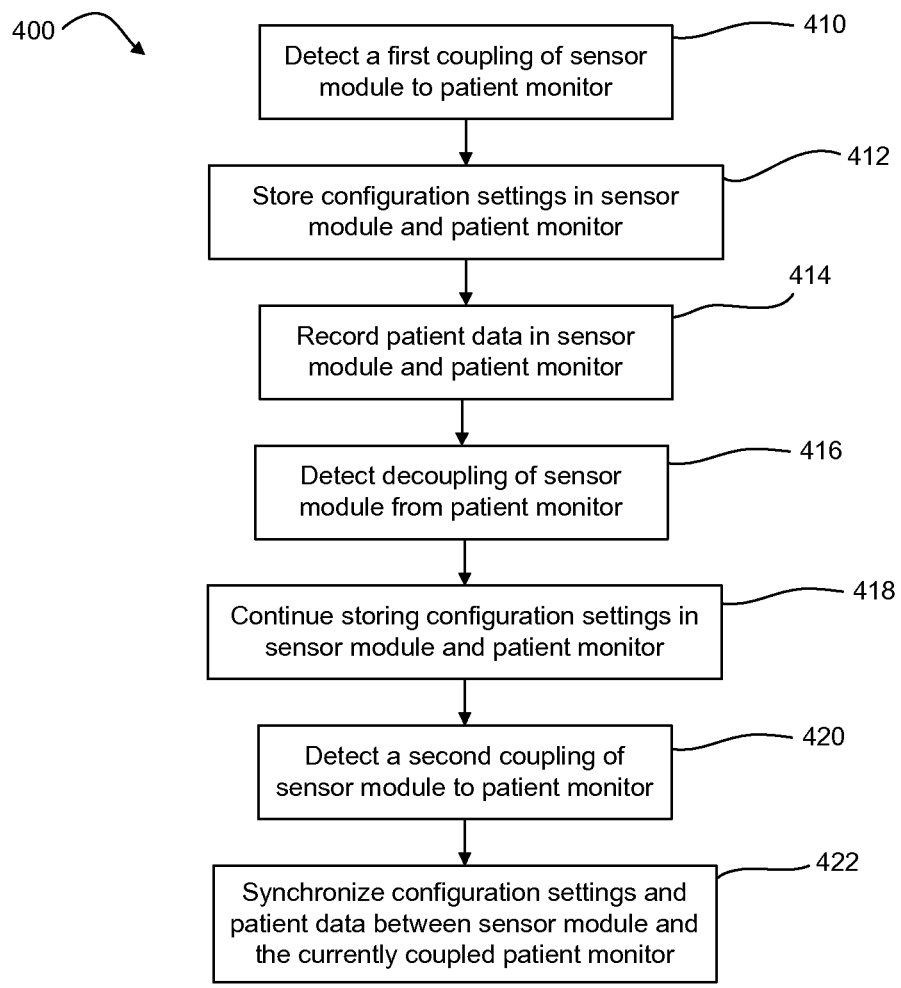
FIG. 4 is a flowchart of a process for synchronizing configuration settings and patient data between a patient monitor and a sensor module according to one embodiment.

FIG. 4 is a flowchart of a process 400 for synchronizing configuration settings and patient data between a patient monitor and a sensor module according to one embodiment. The process 400 includes detecting 410 a first coupling of the sensor module to the patient monitor, storing 412 configuration settings in the sensor module and the patient monitor, and recording 414 patient data in the sensor module and the patient monitor. The process 400 also includes detecting 416 a decoupling of the sensor module from the patient monitor.

After decoupling, the process 400 includes continuing 418 to store patient data in the sensor module (e.g., while the patient is being transported), and detecting 420 a second coupling of the sensor module to a patient monitor. The second coupling may be to the same patient monitor or to a different patient monitor as that of the first coupling. In other words, the second coupling may be a return of the sensor module the original patient monitor in the same ward/bed or it may be a transfer of the sensor module to a different patient monitor located in a different ward/bed. After the second coupling, the method 400 includes synchronizing 422 the configuration settings and patient data between the sensor module and the currently coupled patient monitor.

Figure 5:
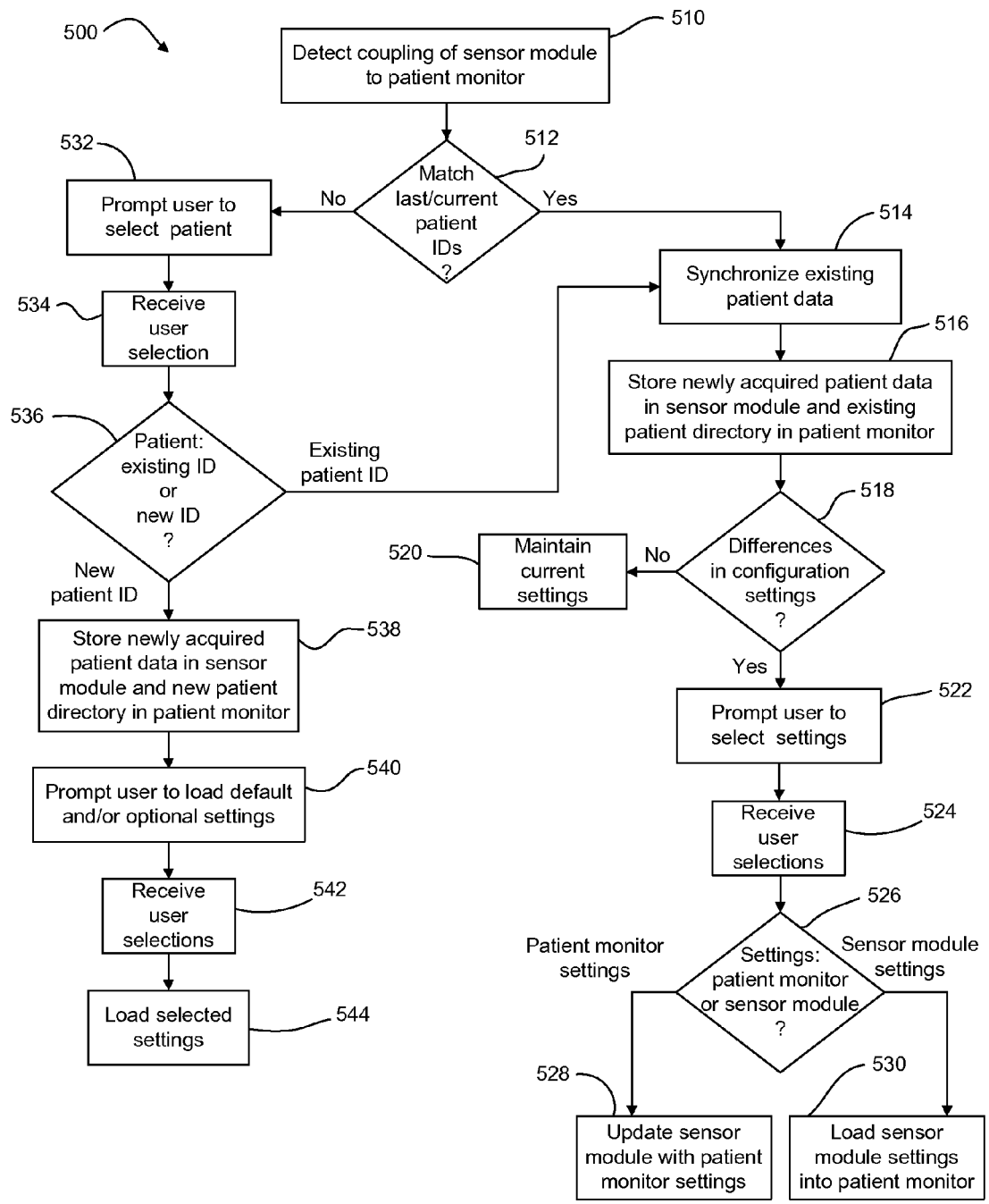
FIG. 5 is a flowchart of a process for synchronizing configuration settings and patient data between a patient monitor and a sensor module according to one embodiment.

FIG. 5 is a flowchart of a process 500 for synchronizing configuration settings and patient data between a patient monitor and a sensor module according to one embodiment. The process 500 includes detecting 510 a coupling of a sensor module to a patient monitor and querying 512 whether there is a match between the last patient ID used in the patient monitor and the current patient ID used in the sensor module. In other words, the system determines whether the sensor module is being reconnected to the patient monitor after returning a particular patient to the corresponding ward or bed.

If there is a match between the last patient ID used in the patient monitor and the current patient ID used in the sensor module, the process 500 includes synchronizing 514 existing patient data between the patient monitor 110 and the sensor module 112. During synchronization, data transferred from the sensor module to the patient monitor is stored in an existing patient directory corresponding to the matched patient ID. The process 400 also stores 516 newly acquired patient data in both the sensor module and in the existing patient directory in the patient monitor.

The process 500 then determines 518 differences in configuration settings stored in the patient monitor and the sensor module. If there are no differences in the configuration settings (e.g., the configuration settings were not changed in either device while they were decoupled from one another), the process 500 includes maintaining 520 the current configuration settings in the patient monitor. If, on the other hand, there are differences in the configuration settings, the process 500 includes prompting 522 the user to select configuration settings, receiving 524 the user selections, and determining 526 whether the user selected the current patient monitor settings or the current sensor module setting. If the user selected the patient monitor settings, then the process 500 includes updating 528 the sensor module with the patient monitor settings. If the user decided to use the sensor module settings, the process 500 includes loading 530 the sensor module settings into the patient monitor.

In certain embodiments, the user may also select a combination of configuration settings from both the current patient monitor settings and the current configuration settings stored in the sensor module. In addition, or in other embodiments, the user may also select one or more default settings (e.g., corresponding to the particular ward). Regardless of the configuration settings actually selected, the patient monitor and the sensor module are synchronized while coupled with each other so as to include the same set of configuration settings.

If there is not a match between the last patient ID used in the patient monitor and the current patient ID used in the sensor module, the process 500 includes prompting 532 the user to select a patient, receiving 534 a user selection, and determining 536 whether the user selected an existing patient ID (e.g., from an index of patient IDs corresponding to at least some patient data already stored in the patient monitor) or a new patient ID.

If the user selected an existing patient ID, the method synchronizes 514 the existing patient data and proceeds as described above. If, on the other hand, the use created a new patient ID, the process 500 stores 538 newly acquired patient data in the sensor module and in a new patient directory in the patient monitor. The process 500 then prompts 540 the user to load default and/or optional configuration settings. The default settings may be associated with particular ward, hospital, or industry standards and may be default settings stored in the patient monitor, a docking station, or on a network server. The optional settings may include configuration settings that are based on the particular patient or user preferences and may be selected, for example, from the configuration settings stored in the sensor module. The process 500 then receives 542 user selections of the configuration settings, and loads the selected configuration settings into both the patient monitor and the sensor module. The patient monitor can then use the configuration settings to analyze and display the patient data and provide desired alarms.

Figure 6:
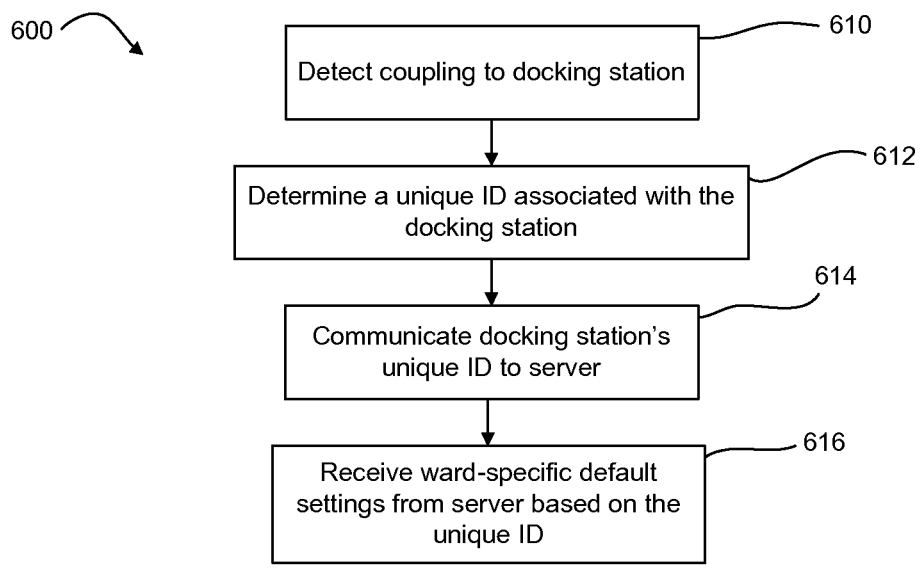
FIG. 6 is a flowchart of a process for updating the configuration settings of a patient monitor from a network server according to one embodiment.

As discussed above, in certain embodiments, default settings associated with a particular monitoring location such as a hospital ward may be acquired through a docking station and/or network. For example, FIG. 6 is a flowchart of a process 600 for updating the configuration settings of a patient monitor from a network server according to one embodiment. The process 600 includes detecting 610 a coupling of a patient monitor to a docking station and determining 612 a unique identifier (ID) associated with the docking station. The unique ID may be stored in the docking station's memory and/or may be a MAC address. The process 600 further includes communicating 614 the docking station's unique ID to the network server and receiving 616 ward-specific default settings from the server based on the unique ID. Certain embodiments of the process 600 may also include determining whether the settings of a particular docking station should be updated and/or querying the user to determine which if any of the ward-specific default settings to load.

In other embodiments, ward-specific default settings may be loaded directly from a server without first determining a unique ID associated with a particular docking station. In certain such embodiments, a user may be able to store settings in, and retrieve settings from, a server regardless of whether or not the patient monitor is even connected to a docking station. For example, a user may choose from a menu of available configurations to load from the server. In addition, after configuring a patient monitor, the user may have the ability to save the configuration directly to the server without a docking station or without associating the configuration with any particular docking station. For example, the user (e.g., a doctor or nurse) may have a preferred configuration that the user does not want to manually create and store on every monitor that the user uses. Instead, the user may save the desired configuration to the server and load it (from the server) onto whichever patient monitor that the user is currently using. This may also be used for setting up the system wherein a user sets up a patient monitor, loads the configuration to the server, goes to the next monitor and downloads the configuration from the server, saves the configuration to the current monitor or docking station, and continues on to the next monitor.

Figure 7:
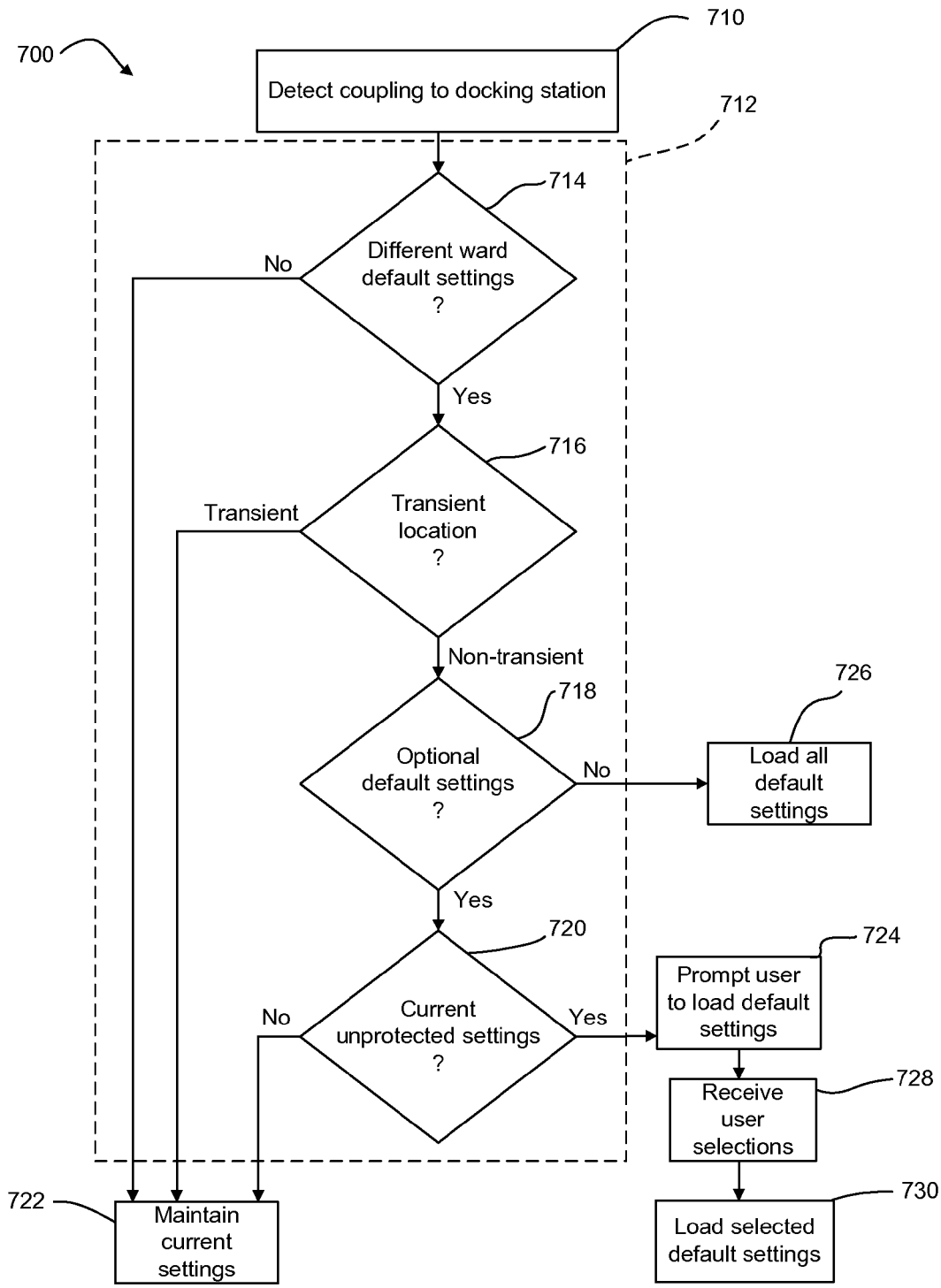
FIG. 7 is a flowchart of a method for use in a patient monitoring system according to other embodiments.

FIG. 7 is a flowchart of a method 700 for use in a patient monitoring system according to other embodiments. The method 700 includes detecting 710 a coupling of a patient monitor to a docking station and determining 712 whether a predetermined condition has been satisfied. In the example embodiment shown in FIG. 7, various options are illustrated for determining 712 whether a predetermined condition has been satisfied. One or more of the different illustrated options 714, 716, 718, 720 may be used in any combination. For example, the method 700 may include querying 714 whether different ward default settings are required as compared to a current set of default settings in the patient monitor. If the ward default settings are not different than the current set of settings in the patient monitor, then the method 700 includes maintaining 722 the current settings of the patient monitor.

The process 700 may also include querying 716 whether the coupled docking station corresponds to a transient location. A transient location may include, for example, a radiology department or other location where a patient may be expected to remain for a relatively short period of time before returning to his or her room or before being transported to another area of the hospital. If the coupled docking station is a transient location, the process 700 includes maintaining 722 the current settings of the patient monitoring system. If the coupled docking station is a non-transient location, the process 700 proceeds toward prompting 724 the user to load the default settings. The process 700 may also include querying 718 whether there are any optional default settings corresponding to the patient monitoring location. If none of the default settings for the patient monitoring location is optional, the process 700 includes loading 726 all of the default settings without prompting the user. The process 700 may also include querying 720 whether any of the current settings are unprotected. If all of the current settings are protected, then the process 700 includes maintaining 722 the current settings of the patient monitoring system. If, on the other hand, one or more of the current settings are unprotected, then the process 700 includes prompting 724 the user to load the default settings. The process 700 further includes receiving 728 user selections indicating which, if any, of the default settings to use, and loading 730 the selected default settings into the patient monitor.

In one embodiment, a user may store a current set of configuration settings to a connected docking station or to a network server by pressing a button on the patient monitor. An artisan will recognize from the disclosure herein that the configuration settings may be stored to other locations or devices other than (or in addition to) the docking station. For example, the configuration settings may be stored in, and retrieved from, a USB flash, a hard drive, or any other type of memory device.

Figure 8:
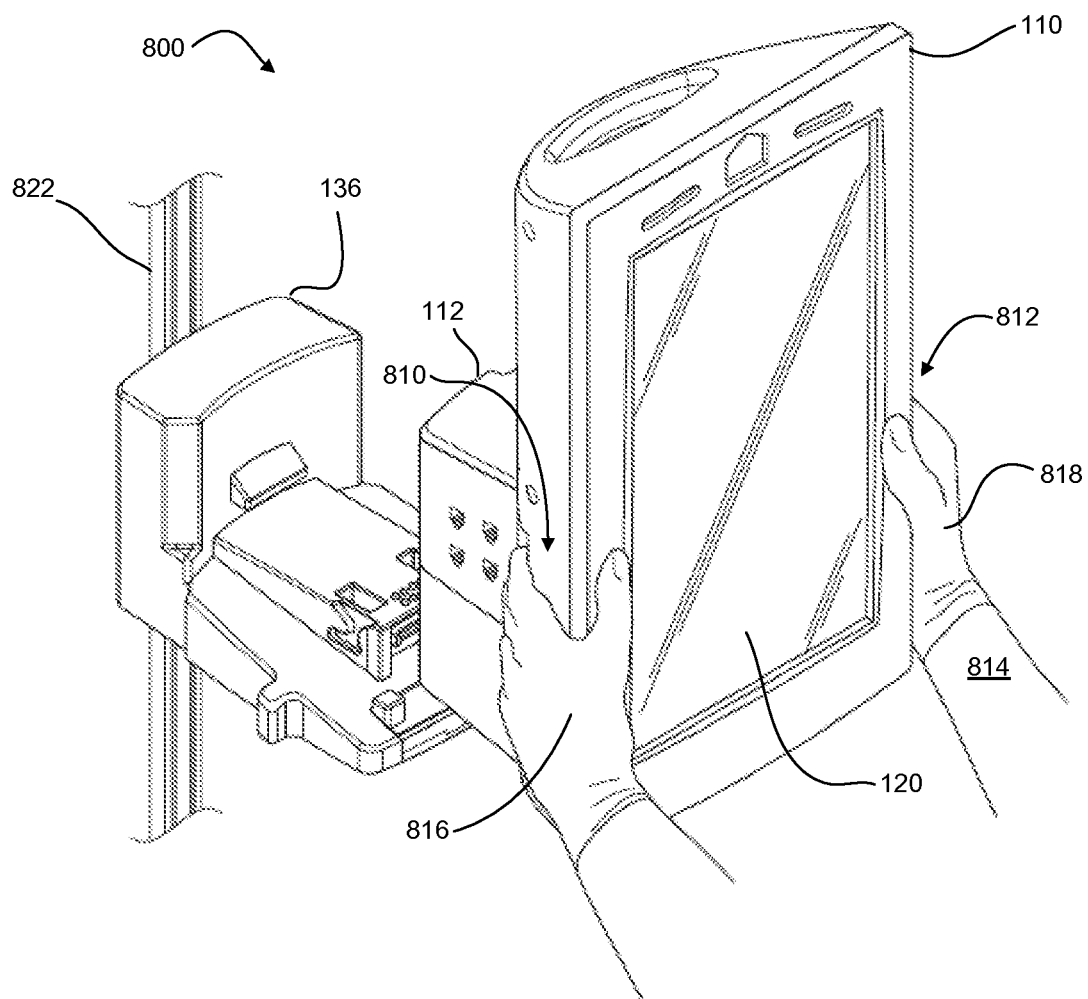
FIG. 8 is a front perspective view of a patient monitor system according to one embodiment.

FIG. 8 is a front perspective view of a patient monitor system 800 according to one embodiment. The embodiment shown in FIG. 8 is provided by way of example and an artisan will understand from the disclosure herein that any patient monitoring system may be used with the embodiments disclosed herein. The system 800 includes a patient monitor 110, a portable sensor module 112, and a docking station 136. The patient monitor 110 may be configured to selectively couple with and decouple from the docking station 136, and the portable sensor module 112 may be configured to selectively couple with and decouple from the patient monitor 110. The coupling between the patient monitor 110 and the docking station 136, or between the portable sensor module 112 and the patient monitor 110, can be mechanical, electrical, optical, and/or any other suitable variety. For example, the coupling can be for physical union, power transfer, and/or communication.

The patient monitor 110 may include one or more gripping regions 810, 812 that are configured to aid in coupling and decoupling the patient monitor 110 from the docking station 136. For example, a medical practitioner 814 can firmly grasp with his or her hands 816, 818 the gripping regions 810, 812 during removal of the patient monitor 110 from the docking station 136. When the patient monitor 110 is separated from the docking station 136, the full weight of the patient monitor 110 can be supported by a grip of the medical practitioner 814 on the gripping regions 810, 812. In some embodiments, the medical practitioner 814 can bear the full weight of the patient monitor 110 by holding only one of the gripping regions 810, 812.

The patient monitoring system 800 may include one or more actuators (not shown) which, when actuated, permit release of the patient monitor 110 from the docking station 136. The actuators can be integrated into the gripping regions 810, 812 or other portions of the patient monitor 110 so as to permit for convenient and continuous-movement dismounting of the patient monitor 110. For example, in some embodiments, a practitioner 814 can actuate an actuator using a hand 816, 818 while that hand 816, 818 is simultaneously holding a respective gripping region 810, 812.

In FIG. 8, the patient monitor 110 is illustrated as having been removed from the docking station 136. A front surface of the patient monitor 122 can include a display 120 that is configured to display information in a visually perceivable format. The screen 120 may be of any suitable variety, including those presently known and those yet to be devised. For example, the screen 120 may include a liquid crystal display (LCD) panel. In some embodiments, the screen 120 may be configured to receive information or otherwise interact with a medical practitioner. For example, the screen 120 may include a touch screen.

In some embodiments, the screen 120 is configured to display information in a predetermined orientation that correlates with a docking orientation of the patient monitor 110. Information can be displayed on the screen 120 in an upright orientation when the patient monitor 110 is coupled with the docking station 136. For example, in the configuration depicted in FIG. 8, text, graphs, or other information can be displayed via the screen 120 in an orientation that is natural for reading.

The patient monitor 110 may include one or more ports for receiving or delivering information, which can include one or more serial ports, USB ports, Ethernet ports, DVI ports, or any other suitable variety of ports, interfaces, or connectors. In addition the patient monitor 110 may include wireless connections (not illustrated), such as 802.11, UWB, Zigbee, Bluetooth, and the like. In some embodiments, information received via one or more of the ports can be displayed on the screen 120.

At least a portion of the information displayed by the patient monitor 120 may represent information received from a patient or that otherwise relates to a patient. For example, in some embodiments, one or more sensors (not shown) are connected to the patient to sense a particular parameter, and information obtained via the one or more sensors is delivered to the portable sensor module 112. The sensors may deliver information to portable sensor module 112 via one or more cables (not shown) connected to one or more ports.

The portable sensor module 112 may be configured to process the information it receives from a sensor and deliver it to patient monitor 110, which can display the processed information. In some embodiments, the patient monitor 110 may further process the information prior to displaying it. The patient monitor 110 may also display information that is independent of the patient, such as, for example, a notification regarding the configuration of the patient monitor 110, or the need to calibrate the portable sensor module 112.

The docking station 136 may be mounted in a substantially fixed position. For example, the docking station 136 may be fixedly mounted to a wall within a hospital room in a single position by one or more plates, brackets, screws, bolts, or other mounting hardware and attachment devices. As another example, the docking station 136 may be configured to transition among multiple fixed positions. For example, in the illustrated embodiment, the docking station 136 is coupled to a mounting strip 822, which is in turn mounted to a wall (not shown) of a hospital room. The docking station 136 is capable of being adjusted upwardly or downwardly along a path constrained by one or more channels defined by the mounting strip 822 so as to transition among a variety of positions. In each such position, the docking station 136 can be fixed relative to the mounting strip 822. In some embodiments, the docking station 136 is coupled with the mounting strip 822 via a mounting plate or a mounting bracket (not shown), the position of which can be adjusted upwardly or downwardly within the channels in any suitable manner.

Figure 9:
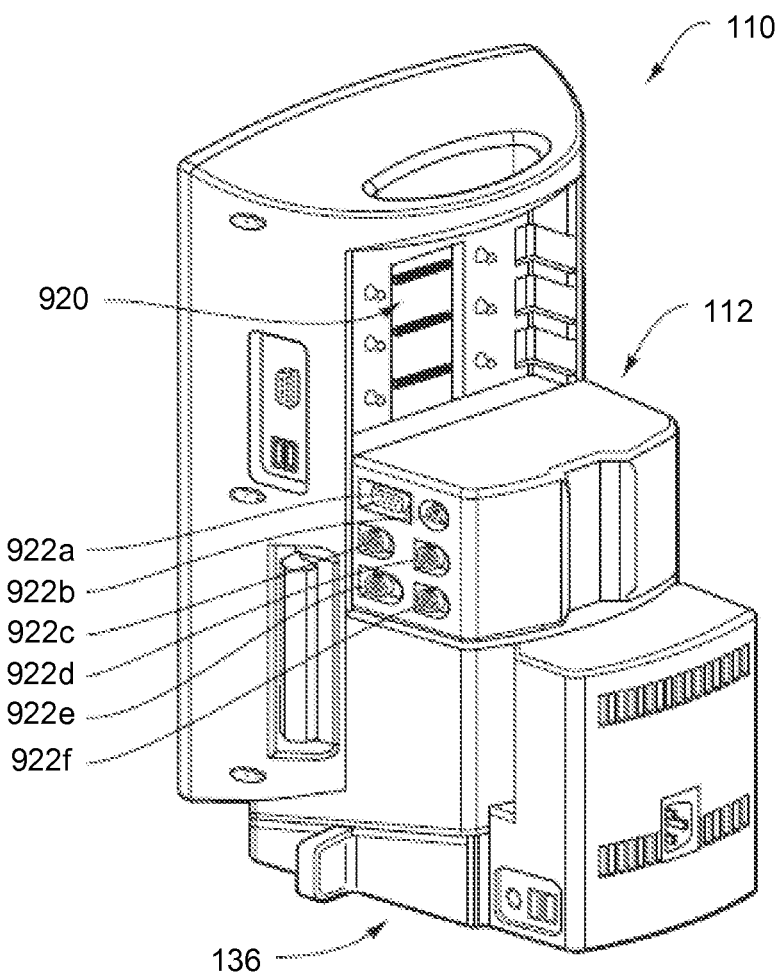
FIG. 9 is a rear perspective view of the patient monitor of FIG. 8 to illustrate the portable sensor module connected to a docking region of the patient monitor according to one embodiment.

FIG. 9 is a rear perspective view of the patient monitor 110 of FIG. 8 to illustrate the portable sensor module 112 connected to a docking region 920 of the patient monitor 110 according to one embodiment. The portable sensor module 112 includes a plurality of connectors or ports 922a, 922b, 922c, 922d, 922e, 922f (referred to collectively as ports 922), which can be configured to couple with one or more wires or cables (not shown). The cables can extend between the ports 522 and one or more sensors (not shown), which can be configured to gather data regarding a patient (not shown).

It will be understood by those having skill in the art that many changes may be made to the details of the above-described embodiments without departing from the underlying principles of the invention. The scope of the present invention should, therefore, be determined only by the following claims.

The invention claimed is:

1. A patient monitor system, comprising:
a patient monitor comprising:
a sensor module interface to receive and process patient data according to a first set of configuration settings;
a first display device to display the patient data according to the first set of configuration settings; and
a first memory device to store the patient data and the first set of configuration settings; and
a portable sensor module configured to selectively couple with and decouple from the sensor module interface of the patient monitor, the portable sensor module configured to receive patient data signals directly from one or more sensors attached to a patient, the portable sensor module comprising:
a patient data acquisition unit for receiving and processing the patient data signals from the one or more sensors and to communicate the processed patient data signals as patient data to the sensor module interface of the patient monitor; and
a second memory device to store the patient data and a second set of configuration settings,
wherein in response to coupling the portable sensor module to the patient monitor, the portable sensor module and the patient monitor communicate with each other to synchronize their respective patient data and to selectively synchronize the first set of configuration settings with the second set of configuration settings, wherein the first set and second set of configuration settings define one or more display settings;
wherein the first memory device comprises a first circular buffer for storing the patient data and the second memory device comprises a second circular buffer for storing the patient data, wherein a circular buffer overwrites newest data over oldest data when the buffer is full, and wherein the patient monitor is configured to synchronize the respective patient data by:
identifying one or more memory blocks in the second circular buffer which includes patient data that is missing from the first circular buffer;
identifying one or more memory blocks in the first circular buffer having a time correspondence with the one or more memory blocks identified in the second circular buffer; and
copying the patient data in the identified one or more memory blocks in the second circular buffer to the identified one or more memory blocks in the first circular buffer.

2. The system of claim 1, wherein the portable sensor module further comprises:
a second display device; and
a user interface,
wherein the second display device and the user interface allow the portable sensor module to operate in a monitor mode that allows a user to view at least some of the second set of configuration settings using the second display device.

3. The system of claim 2, wherein the portable sensor module operating in the monitor mode is further configured to provide an alarm based on the patient data signals and to allow the user to silence the alarm.

4. The system of claim 1, wherein the patient monitor comprises a portable patient monitor.

5. The system of claim 1, wherein the portable sensor module is configured to receive patient data signals directly from the one or more sensors without passing through an intermediate device.

6. The system of claim 1, further comprising a plurality of docking stations that are each associated with a respective monitoring location, wherein each docking station stores default configuration settings associated with its corresponding monitoring location, and when the patient monitor is coupled to a particular docking station the patient monitor is configured to prompt a user to select one or more of the default configuration settings stored in the particular docking station to be part of the first set of configuration settings.

7. The system of claim 1, wherein the patient monitor comprises a first patient monitor, the system further comprising a second patient monitor, wherein the portable sensor module is further configured to be coupled with and decoupled from the second patient monitor, and wherein in response to coupling the portable sensor module to the second patient monitor the second patient monitor copies the patient data signals and the second set of configuration settings stored in the second memory device.

8. The system of claim 1, wherein the first memory device further comprises an index of patient identifiers (IDs) and the second memory device further comprises a patient ID, and wherein the synchronization of the patient data is based on an association of the patient ID stored in the second memory device with the index of patient IDs stored in the first memory device.

9. The system of claim 1, wherein the patient monitor is further configured to selectively synchronize the first set of configuration settings with the second set of configuration settings by:
determining differences between the first set of configuration settings and the second set of configuration settings;
prompting a user to select between the different configuration settings; and
updating the first set of configuration settings according to selections received from the user.

* * * * *